(12) United States Patent
Tada et al.

(10) Patent No.: US 8,008,451 B2
(45) Date of Patent: Aug. 30, 2011

(54) ANTIBODIES TO TNF (TUMOR NECROSIS FACTOR) RECEPTOR FAMILY MEMBERS

(75) Inventors: Hideaki Tada, Osaka (JP); Mikio Konishi, Osaka (JP); Daikichi Fukushima, Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 12/697,676

(22) Filed: Feb. 1, 2010

(65) Prior Publication Data

US 2010/0298546 A1   Nov. 25, 2010

Related U.S. Application Data

(60) Division of application No. 11/935,305, filed on Nov. 5, 2007, now Pat. No. 7,705,140, which is a division of application No. 10/774,378, filed on Feb. 10, 2004, now Pat. No. 7,396,908, which is a continuation of application No. 09/380,276, filed as application No. PCT/JP98/00799 on Feb. 26, 1998, now abandoned.

(30) Foreign Application Priority Data

Feb. 27, 1997 (JP) .................................. 9-043143

(51) Int. Cl.
  *C07K 16/00* (2006.01)
  *C12P 21/08* (2006.01)
(52) U.S. Cl. ............. 530/388.22; 530/387.1; 530/387.9; 530/388.1
(58) Field of Classification Search .................. None
  See application file for complete search history.

(56) References Cited

U.S. PATENT DOCUMENTS 7,223,852 B2   5/2007   Tschopp et al.
2006/0233792 A1  10/2006  Tschopp et al.

FOREIGN PATENT DOCUMENTS

WO         94/01548 A2    1/1994

OTHER PUBLICATIONS

Peer Bork, "Powers and Pitfalls in Sequence Analysis: The 70% Hurdle", Genome Research, 2000, 10:398-400.
Tobias Doerks et al., "Protein annotation: detective work for function prediction", Trends in Genetics, 1998, 14(6):248-250.
Temple F. Smith et al., "The challenges of genome sequence annotation or 'The devil is in the details'", Nature Biotechnology, 1997, 15:1222-1223.
Steven E. Brenner, "Errors in genome annotation", Trends in Genetics, 1999, 15(4):132-133.
Peer Bork, "Go hunting in sequence databases but watch out for the traps", Trends in Genetics, 1996, 12(10):425-427.
A. Gotoh et al., "Stromal cell derived factor-1 suppresses cytokine-induced adhesion to immobilized fibronectin through activation of G-coupled protein in human hematopoietic progenitor cells", Blood, 1997, 90(10):310 Abstract 1378.
Peter Quesenberry et al., "Long-Term Marrow Cultures: Human and Murine Systems", Journal of Cellular Biochemistry, 1991, 45:273-278.
International Search Report issued in PCT/JP98/00799 on Jun. 9, 1998.
Skolnick et al., "From Genes to Protein Structure and Function: Novel Applications of Computational Approaches in the Genomic Era", Trends in Biotechnology, 2000, 34-39.
Takeda, Database EST, Accession No. D82546, Feb. 9, 1996.
Hiller et al., Database EST, Accession No. W56629, Oct. 15, 1996.
Arumugam Jayakumar et al., "Cloning and expression of the multifunctional human fatty acid synthase and its subdomains in *Escherichia coli*", Proc. Natl. Acad. Sci. USA, 1996, 93:14509-14514.
Wadie F. Bahou et al., "cDNA Cloning and Molecular Characterization of MSE55, a Novel Human Serum Constituent Protein That Displays Bone Marrow Stromal/Endothelial Cell-specific Expression", The Journal of Biological Chemistry, 1992, 267(20):13986-13992.
David Wallach, "TNF Ligand and TNFf/NGF Recptor Families", Cytokine Reference, Joost J. Oppenhiem and Marc Feldmann, Editors in Chief, Academic Press (London), 2000, pp. 377-411.
A. Pearce, Database Uniprot_7.2, Accession No. Q5VZF7, May 10, 2005.

*Primary Examiner* — Robert Landsman
(74) *Attorney, Agent, or Firm* — Sughrue Mion, PLLC

(57) ABSTRACT

Polypeptide produced from human stromal cell line, the process for the preparation of the polypeptide, DNA encoding the polypeptide, vector carrying the DNA, host cell transformed by the vector, antibody of the polypeptide, and pharmaceutical composition containing the polypeptide or the antibody.

5 Claims, 1 Drawing Sheet

FIG. 1

```
OAF065   1  ----------  ----------  MALKVLLEQE  KTFF--TLLV  LLGYLSCKVT  CETGDCRQQE    38
hTNFR1   1  -MGLSTVPDL  LLPLVLLELL  VGIYPSGVIG  LVPHLGDREK  RDSV-CPQGK                 48
hTNFR2   1  ----MAPVAV  WAAALAVGLEL WAAA--HALP  AQVAFTPYAP  EPGSTCRLRE                 44
hNGFR    1  ----------  --MGAGATGR  AMDG--PRLL  LLLLLGVSLG  GAKEACPTGL                 36
hFas     1  MLGIWTLLPL  VLTSVARLSS  KSVN--AQVT  DINSKGLELR  KTVTTVETQN                 48
                        *                                                        *
OAF065  39  FRDRSGNCVP  CNQ-CGPGME  LSKECGFGYG  EDAQCVTCRL  HR-FK-EDWG                85
hTNFR1  49  YIHPQNNSIC  CTK-CHKGTY  LYNDCP-GPG  QDTDCRECES  GS-FTASENH                95
hTNFR2  45  YYDQTAQ-MC  CSK-CSPGQH  AKVFC--TKT  SDTVCDSCED  ST-YT-QLWN                88
hNGFR   37  Y-THSGEC--  CKA-CNLGEG  VAQPCGANQT  VCEPCLD-SV  TF-SD-VVSA                79
hFas    49  LEGLHHDGQF  CHKPCPPGER  KARDCTVN-G  DEPDCVPCQE  GKEYT-DKAH                96
                        *                                   *
OAF065  86  F-QCKPCLD-  -CAVVNRFQ-  -KANCSATSDA ICGDCLPGFY  :::                      122
hTNFR1  96  L-RHCLSCSK  -CRKEMGQVE  ISSCTVDRDT  VCG-CRKNQY  :::                      132
hTNFR2  89  WVPECLSCGS  RCSSDQVE--  TQACTREQNR  IC-TCRPGWY  :::                      125
hNGFR   80  T-EPCKPCTE  -CVGLQSM--  SAPCVEADDA  VC-RCAYGYY  :::                      114
hFas    97  FSSKCRRCRL  -CDEGHGLEV  EINCTRTQNT  KC-RCKPNFF  :::                      134
```

ANTIBODIES TO TNF (TUMOR NECROSIS FACTOR) RECEPTOR FAMILY MEMBERS

CROSS-REFERENCE TO RELATED APPLICATIONS

This is a divisional of U.S. patent application Ser. No. 11/935,305 filed Nov. 5, 2007 (now U.S. Pat. No. 7,705,140), which is a Divisional Application of U.S. patent application Ser. No. 10/774,378 filed Feb. 10, 2004 (now U.S. Pat. No. 7,396,908), which is a Continuation Application of U.S. patent application Ser. No. 09/380,276 filed Aug. 27, 1999 (abandoned), which is a National Stage Application filed under §371 of PCT Application No. PCT/JP98/00799 filed Feb. 26, 1998. The entire disclosures of the prior Applications are considered part of the disclosure and are hereby incorporated by reference.

TECHNICAL FIELD

The invention is related to novel polypeptides produced by a certain human stromal cell line and DNAs encoding the said polypeptides.

More particularly, the invention is related to novel polypeptides named to OAF065α and OAF065β (called them OAF065s hereafter), a process for the preparation them, DNAs encoding the said polypeptides, a vector containing the polypeptide, a host cell transformed by the vector, antibody of the said polypeptide, a pharmaceutical composition containing the polypeptide or antibody.

TECHNICAL BACKGROUND

It is known that bone marrow stromal cells form bone marrow micro environment of immunologic, hematopoietic system etc, and they produce and secret essential factors to induce of proliferation and differentiation of stem cells, e.g. IL-7, SCF, IL-11, M-CSF, G-CSF, GM-CSF, IL-6, TGF-β, LIF etc. It is also made clear that a certain bone marrow stromal cells are related to bone metabolism (Kenneth Dorshkind Annu. Rev. Immunol. 8, 111-137. 1990). However, roles of stromal cell are not reconstituted completely from only 25 isolated factors yet. It may suggest that existence of any factors which are not isolated yet.

DISCLOSURE OF THE INVENTION

The present inventors have directed their attention to this point and energetic research has been carried out in order to find novel factors (polypeptides) especially secretory and membrane protein which are generated by a certain stromal cells.

Until now, when a man skilled in the art intends to obtain a particular polypeptide or a DNA encoding it, he generally utilizes methods by confirming an intended biological activity in a tissue or in a cell medium, isolating and purifying the polypeptide and then cloning a gene or methods, by "expression-cloning" with the guidance of the biological activity.

However, physiologically active polypeptides in living body have often many kinds of activities. Therefore, it is increasing that after a gene is cloned, the gene is found to be identical to that encoding a polypeptide already known. Generally bone marrow stromal cell generates only a very slight amount of a factor and it makes difficult to isolate and to purify the factor and to confirm its biological activity.

Recent rapid developments in techniques for constructing cDNAs and sequencing techniques have made it possible to quickly sequence a large amount of cDNAs. By utilizing these techniques, a process, which comprises constructing cDNAs at random, identifying the nucleotide sequences thereof, expressing novel polypeptides encoded by them, is now in progress. Although this process is advantageous in that a gene can be cloned and information regarding its nucleotide sequence can be obtained without any biochemical or genetic analysis, the target gene can be discovered thereby only accidentally in many cases.

The present inventors have studied cloning method of genes coding proliferation and/or differentiation factors functioning in hematopoietic systems and immune systems. Focusing their attention on the fact that most of the secretory proteins such as proliferation and/or differentiation factors (for example various cytokines) and membrane proteins such as receptors thereof (hereafter these proteins will be referred to generally as secretory proteins and the like) have sequences called signal peptides in the N-termini, the inventors conducted extensive studies on a process for efficiently and selectively cloning a gene coding for a signal peptide. Finally, we have successfully invented a screening method for cDNAs having sequence encoding signal peptides, we called the method as signal sequence trap (SST) (See Japanese Patent Application No. 6-13951). We also developed yeast SST method on the same concept. By the method using yeast, genes including sequence encoding signal peptide can be identified more easily and effectively (See U.S. Pat. No. 5,536,637).

By using SST method, the present inventors achieved to find novel membrane proteins produced by bone marrow stromal cell and DNAs encoding them, and we then completed the invention.

The polypeptide OAF065s of the invention are not known one, when amino acid sequences of the polypeptide was compared by a computer to all known sequences in data base of Swiss Prot Release 33. It was found out that the polypeptides of the invention are type-I membrane protein and they have extracellular Cys rich region which commonly exists in the receptor family of Tumor necrosis factor (TNF) (See FIG. 1). So it was suggested that the polypeptides of the invention are novel membrane proteins which belong to TNF receptor family.

BRIEF DESCRIPTION OF THE DRAWING

FIG. 1 shows comparison of the amino acid sequence of the invention and that of TNF receptor family. hTNFR1 (SEQ ID NO: 12) represents human necrosis factor receptor 1, hTNFR2 (SEQ ID NO: 13) represents human necrosis factor receptor 2, Hngfr (SEQ ID NO: 14) represents human nerve growth factor receptor, and hFas (SEQ ID NO: 15) represents human Fas, in this figure.

DETAILED DESCRIPTION OF THE INVENTION

The invention provides:
1) a polypeptide comprising an amino acid sequence shown in SEQ ID NO. 4 or NO. 8,
2) a DNA encoding the polypeptides described above (1),
3) a DNA comprising a nucleotide sequence shown in SEQ ID NO. 1 or NO. 5,
4) a DNA comprising a nucleotide sequence shown in SEQ ID NO. 2 or NO. 6.

More particularly, the invention is concerned with a polypeptide comprising amino acid sequence shown in SEQ ID NO. 4 or NO. 8 in substantially purified form, a homologue thereof, a fragment of the sequence and a homologue of the fragment. Further, the invention is concerned with DNAs encoding the above peptides. More particularly the invention is provided DNAs comprising nucleotide sequence shown in SEQ ID NO. 1, 2, 5 or 6, and DNA containing a fragment which is selectively hybridizing to the DNA comprising nucleotide sequence shown in SEQ ID NO. 1, 2, 5 or 6.

A polypeptide comprising amino acid sequence shown in SEQ ID NO. 4 or 8 in substantially purified form will generally comprise the polypeptide in a preparation in which more than 90%, e.g. 95%, 98% or 99% of the polypeptide in the preparation is that of the SEQ ID NO. 4 or 8. A homologue of polypeptide comprising amino acid sequence shown in SEQ ID NO. 4 or 8 will be generally at least 70%, preferably at least 80 or 90% and more preferably at least 95% homologous to the polypeptide comprising amino acid sequence shown in SEQ ID NO. 4 over a region of at least 20, preferably at least 30, for instance 40, 60 or 100 more contiguous amino acids. Such a polypeptide homologue will be referred to a polypeptide of the invention.

Generally, a fragment of polypeptide comprising amino acid 25 sequence shown in SEQ ID NO. 4 or 8 or its homologues will be at least 10, preferably at least 15, for example 20, 25, 30, 40, 50 or 60 amino acids in length, and are also referred to by the term "a polypeptide of the invention".

A DNA capable of selectively hybridizing to the DNA comprising nucleotide sequence shown in SEQ ID NO. 1, 2, 5 or 6 will be generally at least 70%, preferably at least 80 or 90% and more preferably at least 95% homologous to the DNA comprising nucleotide sequence shown in SEQ ID NO. 1, 2, 5 or 6 over a region of at least 20, preferably at least 30, for instance 40, 60 or 100 or more contiguous nucleotides. Such DNA will be referred to "a cDNA of the invention".

Fragments of the DNA comprising nucleotide sequence shown in SEQ ID NO. 1, 2, 5 or 6 will be at least 10, preferably at least 15, for example 20, 25, 30 or 40 nucleotides in length, and will be also referred to "a DNA of the invention" as used herein.

A further embodiment of the invention provides replication and expression vectors carrying DNA of the invention. The vectors may be, for example, plasmid, virus or phage vectors provided with an origin of replication, optionally a promoter for the expression of the said DNA and optionally a regulator of the promoter. The vector may contain one or more selectable marker genes, for example a ampicillin resistance gene. The vector may be used in vitro, for example of the production of RNA corresponding to the cDNA, or used to transfect or transfect a host cell.

A further embodiment of the invention provides host cells transformed with the vectors for the replication and expression of the DNA of the invention, including the DNA SEQ ID NO. 1, 2, 5 or 6 or the open reading frame thereof. The cells will be chosen to be compatible with the vector and may for example be bacterial, yeast, insect or mammalian.

A further embodiment of the invention provides a method of producing a polypeptide which comprises culturing host cells of the invention under conditions effective to express a polypeptide of the invention. Preferably, in addition, such a method is carried out under conditions in which the polypeptide of the invention is expressed and then produced from the host cells.

DNA of the invention may also be inserted into the vectors described above in an antisense orientation in order to proved for the production of antisense RNA. Such antisense RNA may be used in a method of controlling the levels of a polypeptide of the invention in a cell.

The invention also provides monoclonal or polyclonal antibodies against a polypeptide of the invention. The invention further provides a process for the production of monoclonal or polyclonal antibodies to the polypeptides of the invention. Monoclonal antibodies may be prepared by common hybridoma technology using polypeptides of the invention or fragments thereof, as an immunogen. Polyclonal antibodies may also be prepared by common means which comprise inoculating host animals, for example a rat or a rabbit, with polypeptides of the invention and recovering immune serum.

The invention also provides pharmaceutical compositions containing a polypeptide of the invention, or an antibody thereof, in association with a pharmaceutically acceptable diluent and/or carrier.

The polypeptide of the invention includes that which a part of their amino acid sequence is lacking (e.g., a polypeptide comprised of the only essential sequence for revealing a biological activity in an amino acid sequence shown in SEQ ID NO. 4), that which a part of their amino acid sequence is replaced by other amino acids (e.g., those replaced by an amino acid having a similar property) and that which other amino acids are added or inserted into a part of their amino acid sequence, as well as those comprising the amino acid sequence shown in SEQ ID NO. 4 or 8.

As known well, there are one to six kinds of codon as that encoding one amino acid (for example, one kind of codon for Methioine (Met), and six kinds of codon for leucine (Leu) are known). Accordingly, the nucleotide sequence of DNA can be changed in order to encode the polypeptide having the same amino acid sequence.

The DNA of the invention, specified in (2) includes a group of every nucleotide sequences encoding polypeptides (1) shown in SEQ ID NO. 4 or 8. There is a probability that yield of a polypeptide is improved by changing a nucleotide sequence.

The DNA specified in (3) is the embodiment of the DNA shown in (2), and indicate the sequence of natural form.

The DNA shown in (4) indicates the sequence of the DNA specified in (3) with natural non-translational region.

cDNA carrying nucleotide sequence shown in SEQ ID NO. 2 is prepared by the following method:

Brief description of Yeast SST method (see U.S. Pat. No. 5,536,637) is as follows.

Yeast such as *Saccharomyces cerevisiae* should secrete invertase into the medium in order to take sucrose or raffinose as a source of energy or carbon (Invertase is an enzyme to cleave raffinose into sucrose and melibiose, sucrose into fructose and glucose). It is known that many known mammalian signal sequence make yeast secrete its invertase. From these knowledge, SST method was developed as a screening method to find novel signal sequence which make it possible can to secrete yeast invertase from mammalian cDNA library. SST method uses yeast growth on raffinose medium as a marker. Non-secretory type invertase gene SUC2 (GEN-BANK Accession No. V 01311) lacking initiation codon ATG was inserted to yeast expression vector to prepare yeast SST vector pSUC2. In this expression vector, ADH promoter, ADH terminator (both were derived from AAH5 plasmid (Gammerer, Methods in Enzymol. 101, 192-201, 1983)), 2µ on (as a yeast replication origin), TRP1 (as a yeast selective marker), ColE1 ori (as a *E. Coli* replication origin) and ampicillin resistance gene (as a drug resistance marker) were inserted. Mammalian cDNA was inserted into the upstream of SUC2 gene to prepare yeast SST cDNA library. Yeast lacking secretory type invertase, was transformed with this library. If inserted mammalian cDNA encodes a signal peptide, yeast could be survive in raffinose medium as a result of restoring secretion of invertase. Only to culture yeast colonies, prepare plasmids and determine the nucleotide sequence of the insert cDNAs, it is possible to identify novel signal peptide rapidly and easily.

Preparation of yeast SST cDNA library is as follows:
(1) mRNA is isolated from the targeted cells, second-strand synthesis is performed by using random primer with certain restriction enzyme (enzyme I) recognition site,
(2) double-strand cDNA is ligated to adapter containing certain restriction endonuclease (enzyme II) recognition site, differ from enzyme I, digested with enzyme I and fractionated in a appropriate size,
(3) obtained cDNA fragment is inserted into yeast expression vector on the upstream region of invertase gene which signal peptide is deleted and the library was transformed.

Detailed description of each step is as follows:
(1) mRNA is isolated from mammalian organs and cell lines stimulate them with appropriate stimulator if necessary) by known methods (Molecular Cloning (Sambrook, J., Fritsch, E. F. and Maniatis, T., Cold Spring Harbor Laboratory Press, 1989) or Current Protocol in Molecular Biology (F. M. Ausubel et al, John Wiley & Sons, Inc.) if not remark especially).

HAS303 (human bone marrow stromal cell line: provide from Professor Keisuke Sotoyama, Dr. Makoto Aizawa of Tokyo Medical College, 1st medicine; see J. Cell. Physiol., 148, 245-251, 1991 and Experimental Hematol., 22, 482-487, 1994) and HUVEC (human umbilical vein cord endothelial cell: ATCC No. CRL-1730) are chosen as a tissue source. Double-strand cDNA synthesis using random primer is performed by known methods.

Any sites may be used as restriction endonuclease recognition site I which is linked to adapter and restriction endonuclease recognition site II which is used in step (2), if both sites are different each other. Preferably, EcoRI is used as enzyme I and XhoI as enzyme II.

In step (2) cDNA is created blunt-ends with T4 DNA polymerase, ligated enzyme II adapter and digested with enzyme I. Fragment cDNA is analyzed with agarose-gel electrophoresis (AGE) and is selected cDNA fraction ranging in size from 300 to 800 bp. As mentioned above, any enzyme may be used as enzyme II if it is not same the enzyme I.

In step (3), cDNA fragment obtained in step (2) is inserted into yeast expression vector on the upstream region of invertase gene which signal peptide is deleted. E. coli transformed with the expression vector. Many vectors are known as yeast expression plasmid vector. For example, YEp24 is also functioned in E. Coli. Preferably pSUC2 as described above is used.

Many host E. Coli strains are known for transformation, preferably DH10B competent cell is used. Any known transformation method is available, preferably it is performed by electropolation method. Transformant is cultured by conventional methods to obtain cDNA library for yeast SST method.

However not every All of the clones do not contain cDNA fragment. Further all of the gene fragments do not encode unknown signal peptides. It is therefore necessary to screen a gene fragment encoding for an unknown signal peptide from the library.

Therefore, screening of fragments containing a sequence encoding an appropriate signal peptide is performed by transformation of the cDNA library into *Saccharomyces cerevisiae* (e.g. YT455 strain) which lack invertase (it may be prepared by known methods). Transformation of yeast is performed by known methods, e.g. lithium acetate method. Transformant is cultured in a selective medium, then transferred to a medium containing raffinose as a carbon source. Survival colonies are selected and then prepared plasmid. Survival colonies on a raffinose-medium indicates that some signal peptide of secretory protein was inserted to this clone.

Isolated positive clones is determined the nucleotide sequence. As to a cDNA encodes unknown protein, full-length clone may be isolated by using cDNA fragment as a probe and then determined to obtain full-length nucleotide sequence. These manipulation is performed by known methods.

Once the nucleotide sequences shown in SEQ ID NO. 1, 2, 5 or 6 are determined partially or preferably fully, it is possible to obtain DNA encode mammalian protein itself, homologue or subset. cDNA library or mRNA derived from mammals was screened by PCR with any synthesized oligonucleotide primers or by hybridization with any fragment as a probe. It is possible to obtain DNA encodes other mammalian homologue protein from other mammalian cDNA or genome library.

If a cDNA obtained above contains a nucleotide sequence of cDNA fragment obtained by SST (or consensus sequence thereof), it will be thought that the cDNA encodes signal peptide. So it is clear that the cDNA will be full-length or almost full.

(All signal sequences exist at N-termini of a protein and are encoded at 5'-termini of open reading frame of cDNA.)

The confirmation may be carried out by Northern analysis with the said cDNA as a probe. It is thought that the cDNA is almost complete length, if length of the cDNA is almost the same length of the mRNA obtained in the hybridizing band.

Once the nucleotide sequences shown in SEQ ID NOs. 1, 2, 5 or 6 are determined, DNAs of the invention are obtained by chemical synthesis, or by hybridization making use of nucleotide fragments which are chemically synthesized as a probe. Furthermore, DNAs of the invention are obtained in desired amount by transforming a vector that contains the DNA into a proper host, and culturing the transformant.

The polypeptides of the invention may be prepared by:
(1) isolating and purifying from an organism or a cultured cell,
(2) chemically synthesizing, or
(3) using recombinant DNA technology, preferably, by the method described in (3) in an industrial production.

Examples of expression system (host-vector system) for producing a polypeptide by using recombinant DNA technology are the expression systems of bacteria, yeast, insect cells and mammalian cells.

In the expression of the polypeptide, for example, in *E. Coli*, the expression vector is prepared by adding the initiation codon (ATG) to 5' end of a DNA encoding mature peptide, connecting the DNA thus obtained to the downstream of a proper promoter (e.g., trp promoter, lac promoter, λ PL promoter, T7 promoter etc.), and then inserting it into a vector (e.g., pBR322, pUC18, pUC19 etc.) which functions in an *E. coli* strain.

Then, an *E. coli* strain (e.g., *E. coli* DH1 strain, *E. coli* JM109 strain, *E. coli* 53101 strain, etc.) which is transformed with the expression vector described above may be cultured in a appropriate medium to obtain the desired polypeptide. When a signal peptide of bacteria (e.g., signal peptide of pel B) is utilized, the desired polypeptide may be also released in periplasm. Furthermore, a fusion protein with other polypeptide may be also produced easily.

In the expression of the polypeptide, for example, in a mammalian cells, for example, the expression vector is prepared by inserting the DNA encoding nucleotide shown in SEQ ID NO. 2 or 6 into the downstream of a proper promoter (e.g., SV40 promoter, LTR promoter, metallothionein promoter etc.) in a proper vector (e.g., retrovirus vector, papilloma virus vector, vaccinia virus vector, SV40 vector, etc.). A proper mammalian cell (e.g., monkey COS-7 cell, Chinese hamster CHO cell, mouse L cell etc.) is transformed with the expression vector thus obtained, and then the transformant is cultured in a proper medium to get a desired polypeptide on the cell membrane. A vector described above can be inserted with deletion mutant DNA that encodes sequence, which is deleted transmembrane region from SEQ ID NOs. 2 or 6 and the expression vector can be transfected into an appropriate mammalian cell. The aimed soluble protein can be secreted into the culture medium. The polypeptide available by the way described above can be isolated and purified by conventional biochemical method.

INDUSTRIAL APPLICABILITY

The polypeptide OAF065s of the invention show significant homology with a series of proteins which belong to TNF receptor family. Proteins, which belong to TNF receptor family, are type-1 membrane protein which have 3 to 6 repeated structure containing 6 Cys residues in the extracellular domain. It has been apparent that the proteins are related to proliferation, differentiation cell death of various cells by the interaction with ligand thereof (Craig A: Smith et. al., Cell, 76, 959-962, 1994). For instance, Neuronal growth factor (NGF) receptor/NGF are essential for keeping several kinds of neuronal cells surviving, allowing neuronal tubes to elongate and promoting to make neuronal transmitters (Chao M. V., J. Neurobiol., 25, 1373-1385, 1994). Fas/FasL is essential for maintaining homeostasis in vivo, such as destruction of cancer cells and removal of auto-reactive lymphocytes via its apoptosis-inducing activity, and also relates to CD4-positive T cell reduction in AIDS, fulminant hepatitis; graft versus host disease (GVHD) after transplantation and the onset of various autoimmune diseases (Nagata S. et. al., Science, 267, 1449-1456, 1995). CD40/CD40L is essential for activating B cells (acceleration of growth and antibody production) via T/5 cell interaction (Banchereau J. et. al., Annu. Rev. Immunol., 12, 881-922, 1994). TNF receptor/TNF and lymphotoxin (LT) receptor/LT have activities, such as growth, activation and differentiation induction of various immune and hematopoietic cells, cytotoxicity and growth inhibition of tumor cells, growth and activation of various connective tissues (e.g., endothelial cells, fibroblasts, osteoblasts, etc.) and viral growth inhibition, and are also essential for the morphology or organ formation of lymphoid tissue (Ware C. F. et al., Curr. Topics Microbiol. Immunol., 198, 175-218, 1995).

Since repetitive structures of Cys are present at three points in the extracellular domain of the polypeptide of the invention, it is obvious that this is a novel protein belonging to the TNF receptor family and exerts its activity via a ligand belonging to a known or unknown TNF family. In consequence, it is considered that the polypeptide of the invention and a cDNA molecule which encodes the polypeptide will show one or more of the effects or biological activities (including those which relates to the assays cited below) concerning differentiation, proliferation, growth, survival or cell death of hematopoietic, immune and nerve system cells, immune system functions, proliferation and growth of tumor, inflammations, bone metabolism, etc. The effects or biological activities described in relation to the polypeptide of the invention are provided by administration or use of the polypeptide or by administration or use of a cDNA molecule which encodes the polypeptide (e.g., vector suitable for gene therapy or cDNA introduction).

1) Cytokine Activity and Cell Proliferation/Differentiation Activity

The polypeptide of the invention may exhibit cytokine, cell proliferation (either inducing or inhibiting) or cell differentiation (either inducing or inhibiting) activity or may induce production of other cytokines in certain cell populations. Many protein factors discovered to date, including all known cytokines, have exhibited activity in one or more factor dependent cell proliferation assays, and hence the assays serve as a convenient confirmation of cytokine activity. The activity of a polypeptide of the invention is evidenced by any one of a number of routine factor dependent cell proliferation assays for cell lines.

2) Immune Stimulating/Suppressing Activity

The polypeptide of the invention may also exhibit immune stimulating or immune suppressing activity. The polypeptide of the invention may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g. HIV) as well as bacterial or fungal infections, or may result from autoimmune disorders. More specifically, infectious diseases causes by viral, bacterial, fungal or other infection may be treatable using the polypeptide of the invention, including infections by HIV, hepatitis viruses, herpes viruses, mycobacteria, leshmania, malaria and various fungal infections such as candida. Of course, in this regard, a polypeptide of the invention may also be useful where a boost to the immune system generally would be indicated, i.e., in the treatment of cancer.

Such a polypeptide of the invention may also to be useful in the treatment of allergic reactions and conditions, such as asthma or other respiratory problems.

The polypeptide of the invention may also suppress chronic or acute inflammation, such as, for example, that associated with infection (such as septic shock or systemic inflammatory response syndrome (SIRS)), inflammatory bowel disease, Crohn's disease or resulting from over production of cytokines such as TNF or IL-1 (such as the effect demonstrated by IL-11).

3) Hematopoiesis Regulating Activity

The polypeptide of the invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis.

The said biological activities are concerned with the following all or some example(s). e.g. in supporting the growth and proliferation of erythroid progenitor cells alone or in combination with other cytokines, thereby indicating utility. for example, in treating various anemias or for use in conjunction with irradiation/chemotherapy to stimulate the production of erythroid precursors and/or erythroid cells;

in supporting the growth and proliferation of myeloid cells such as granulocytes and monocytes/macrophages (i.e., traditional CSF activity) useful, for example, in conjunction with chemotherapy to prevent or treat consequent myelosuppression;

in supporting the growth and proliferation of megakaryocytes and consequently of platelets thereby allowing prevention or treatment of various platelet disorders such as thrombocytopenia, and generally for use in place of or complimentary to platelet transfusions;

and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e. in conjunction with bone marrow transplantation) as normal cells or genetically manipulated for gene therapy.

The activity of the polypeptide of the invention may, among other means. be measured by the following methods:

4) Tissue Generation/Regeneration Activity

The polypeptide of the invention also may have utility in compositions used for bone, cartilage, tendon, Ligament and/or nerve tissue growth or regeneration, as well as for wound healing and tissue repair, and in the treatment of bums, incisions and ulcers. The polypeptide of the invention, which induces cartilage and/or bone growth in circumstances where bone is not normally formed, has application in the healing of bone fractures and cartilage damage or defects in humans and other animals. Such a preparation employing the polypeptide of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

The polypeptide of this invention may also be used in the treatment of periodontal disease, and in other tooth repair processes. Such agents may provide an environment to attract bone-forming cells, stimulate growth of bone-forming cells or induce differentiation of progenitors of bone-forming cells. The polypeptide of the invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes.

Another category of tissue regeneration activity that, may be attributable to the polypeptide of the invention is tendon/ligament formation. A polypeptide of the invention, which induces tendon/ligament-like tissue or other tissue formation in circumstances where such tissue is not normally formed, has application in the healing of tendon or ligament tears, deformities and other tendon or ligament defects in humans and other animals. Such a preparation employing a tendon/Ligament-like tissue inducing polypeptide may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the invention contributes to the repair of congenital, trauma induced, or other tendon or ligament defects of other origin, and is also useful in cosmetic plastic surgery for attachment or repair of tendons or ligaments. The compositions of the invention may provide an environment to attract tendon- or ligament-forming cells, stimulate growth of tendon- or ligament-forming cells, induce differentiation of progenitors of tendon- or ligament-forming cells, or induce growth of tendon Ligament cells or progenitors ex vivo for return in vivo to effect tissue repair. The compositions of the invention may also be useful in the treatment of tendinitis, carpal tunnel syndrome and other tendon or ligament defects. The compositions may also include an appropriate matrix and/or sequestering agent as a carrier as is well known in the art.

The polypeptide of the invention may also be useful for proliferation of neural cells and for regeneration of nerve and brain tissue. i.e. for the treatment of central and peripheral nervous system diseases and neuropathies. as well as mechanical and traumatic disorders, which involve degeneration, death or trauma to neural cells or nerve tissue. More specifically, the polypeptide of the invention may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the invention include mechanical and traumatic disorders, such as spinal cord disorders, head trauma and cerebrovascular diseases such as stroke. Peripheral neuropathies resulting from chemotherapy or other medical therapies may also be treatable using the polypeptide of the invention.

It is expected that the polypeptide of the invention may also exhibit activity for generation of other tissues, such as organs (including, for example, pancreas, liver, intestine, kidney, skin, endothelium), muscle (smooth, skeletal or cardiac) and vascular (including vascular endothelium) tissue, or for promoting the proliferation of cells comprising such tissues. Part of the desired effects may be by inhibition of fibrotic scarring to allow normal tissue to regenerate.

A polypeptide of the invention may also be useful for gut protection or regeneration and treatment of lung or liver fibrosis, reperfusion injury in various tissues, and conditions resulting from systemic cytokine damage.

5) Activin/Inhibin Activity

The polypeptide of the invention may also exhibit activin- or inhibin-related activities. Inhibins are characterized by their ability to inhibit the release of follicle stimulating hormone (FSH), while activins and are characterized by their ability to stimulate the release of follicle stimulating hormone (FSH). Thus, a polypeptide of the invention alone or in heterodimers with a member of the inhibin α family, may be useful as a contraceptive based on the ability of inhibins to decrease fertility in female mammals and decrease spermatogenesis in male mammals. Administration of sufficient amounts of other inhibins can induce infertility in these mammals. Alternatively, the polypeptide of the invention, as a homodimer or as a heterodimer with other protein subunits of the inhibin-β group, may be useful as a fertility inducing therapeutic, based upon the ability of activin molecules in stimulating FSH release from cells of the anterior pituitary. See for example, U.S. Pat. No. 4,798,885. The polypeptide of the invention may also be useful for advancement of the onset of fertility in sexually immature mammals, so as to increase the lifetime reproductive performance of domestic animals such as cows, sheep and pigs.

6) Chemotactic/Chemokinetic Activity

A polypeptide of the invention may have chemotactic or chemokinetic activity (e.g. act as a chemokine) for mammalian cells, including. for example. monocytes, neutrophils, T-cells, mast cells, eosinophils and/or endothelial cells. Chemotactic and chemokinetic proteins can be used to mobilized or attract a desired cell population to a desired site of action. Chemotactic or chemokinetic proteins provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

7) Hemostatic and Thrombolytic Activity

The polypeptide of the invention may also exhibit hemostatic or thrombolyic activity. As a result, such a protein is expected to be useful in treatment of various coagulation disorders (including hereditary disorders, such as hemophilias) or to enhance coagulation and other hemostatic events in treating wounds resulting from trauma, surgery or other causes. A protein of the invention may also be useful for dissolving or inhibiting formation of thromboses and for treatment and prevention of conditions resulting therefrom (such as. for example, infarction or stroke).

8) Receptor/Ligand Activity

The polypeptide of the invention may also demonstrate activity as receptors, receptor ligands or inhibitors or agonists of receptor/ligand interactions. Examples of such receptors and ligands include, without limitation, cytokine receptors and their ligands, receptor kinases and their ligands, receptor phosphatases and their ligands, receptors involved in cell-cell interactions and their ligands (including cellular adhesion molecules (such as selectins, integrins and their ligands) and receptor/ligand pairs involved in antigen presentation, antigen recognition and development of cellular and humoral immune responses). Receptors and ligands are also useful for screening of potential peptide or small molecule inhibitors of the relevant receptor/ligand interaction. A polypeptide of the invention (including, without limitation, fragments of receptors and ligands) may themselves be useful as inhibitors of receptor/ligand interactions.

9) Other Activity

The polypeptide of the invention may also exhibit one or more of the following additional activities or effects: inhibiting the growth, infection or function of, or killing, infectious agents, including, bacteria, viruses, fungi and other parasites; effecting (suppressing or enhancing) bodily characteristics, including, height, weight, hair color, eye color, skin, fat to lean ratio or other tissue pigmentation, or organ or body part size or shape (such as, for example, breast augmentation or diminution); effecting elimination of dietary fat, protein, carbohydrate; effecting behavioral characteristics, including appetite, libido, stress, cognition (including cognitive disorders), depression and violent behaviors;

providing analgesic effects or other pain reducing effects; promoting differentiation and growth of embryonic stem cells in lineages other than hematopoietic lineages;

in the case of enzymes, correcting deficiencies of the enzyme and treating deficiency-related diseases.

The polypeptide with above activities, is suspected to have following functions by itself or interaction with its ligands or receptors or association with other molecules. For example, proliferation or cell death of B cells, T cells and/or mast cells or class specific induction of B cells by promotion of class switch of immunoglobulin genes; differentiation of B cells to antibody-forming cells; proliferation, differentiation, or cell death of precursors of granulocytes; proliferation, differentiation, or cell death of precursors of monocytes-macrophages;

proliferation, of up regulation or cell death of neutrophils, monocytes-macrophages, eosinophils and/or basophils; proliferation, or cell death of precursors of megakaryocytes; proliferation, differentiation, or cell death of precursors of neutrophils; proliferation, differentiation, or cell death of precursors of T cells and B cells; promotion of production of erythrocytes; sustainment of proliferation of erythrocytes, neutrophils, eosinophils, basophils, monocytes-macrophages, mast cells, precursors of megakaryocyte; promotion of migration of neutrophils, monocytes-macrophages, B cells and/or T cells; proliferation or cell death of thymocytes; suppression of differentiation of adipocytes; proliferation or cell death of natural killer cells;

proliferation or cell death of hematopoietic stem cells; suppression of proliferation of stem cells and each hematopoietic precursor cells; promotion of differentiation from mesenchymal stem cells to osteoblasts or chondrocytes, proliferation or cell death of mesenchymal stem cells, osteoblasts or chondrocytes and promotion of bone absorption by activation of osteoclasts and promotion of differentiation from monocytes to osteoclasts.

This peptide is also suspected to function to nervous system, so expected to have functions below; differentiation to kinds of neurotransmitter-responsive neurons, survival or cell death of these cells; promotion of proliferation or cell death of glial cells; spread of neural dendrites; survival or cell death of gangriocytes; proliferation, promotion of differentiation, or cell death of astrocytes; proliferation or survival of peripheral neurons; proliferation or cell death of Schwann cells; proliferation, survival or cell death of motoneurons.

Furthermore, in the process of development of early embryonic, this polypeptide is expected to promote or inhibit the organogenesis of epidermis, brain, backbone, and nervous system by induction of ectoderm, that of notochord connective tissues (bone, muscle, tendon), hemocytes, heart, kidney, and genital organs by induction of mesoderm, and that of digestive apparatus (stomach, intestine, liver, pancreas), respiratory apparatus (lung, trachea) by induction of endoderm. In adult, also, this polypeptide is thought to proliferate or inhibit the above organs.

Therefore, this polypeptide itself is expected to be used as an agent for the prevention or treatment of disease of progression or suppression of immune, nervous, or bone metabolic function, hypoplasia or overgrowth of hematopoietic cells: inflammatory disease (rheumatism, ulcerative colitis, etc.), decrease of hematopoietic stem cells after bone marrow transplantation, decrease of leukocytes, platelets, B-cells, or T-cells after radiation exposure or chemotherapeutic dosage against cancer or leukemia, anemia, infectious disease, cancer, leukemia, AIDS, bone metabolic disease (osteoporosis etc.), various degenerative disease (Alzheimer's disease, multiple sclerosis, etc.), or nervous lesion.

In addition, since this polypeptide is thought to induce the differentiation or growth of organs derived from ectoderm, mesoderm, and endoderm, this polypeptide is expected to be an agent for tissue repair (epidermis, bone, muscle, tendon, heart, kidney, stomach, intestine, liver, pancreas, lung, and trachea, etc.).

Quantitation of the polypeptide of the invention in the body can be performed using polyclonal or monoclonal antibodies against the polypeptide of the invention. It can be used the study of relationship between this polypeptide and disease or diagnosis of disease, and so on. Polyclonal and monoclonal antibodies can be prepared using this polypeptide or its fragment as an antigen by conventional methods.

Identification, purification or molecular cloning of known or unknown proteins which bind the polypeptide of the invention (preferably polypeptide of extracellular domain) can be performed using the polypeptide of the invention by, for example, preparation of the affinity-column.

Identification of the downstream signal transmission molecules which interact with the polypeptide of the invention in cytoplasma and molecular cloning of the gene can be performed:

by west-western method using the polypeptide of the invention (preferably polypeptide of transmembrane region or intracellular domain) or by yeast two-hybrid system using the cDNA (preferably cDNA encoding transmembrane region or cytoplasmic domain of the polypeptide).

Agonists/antagonists of this receptor polypeptide and inhibitors between receptor and signal transduction molecules can be screened using the polypeptide of the invention.

cDNAs of the invention are useful not only the important and essential template for the production of the polypeptide of the invention which is expected to be largely useful, but also be useful for diagnosis or therapy (for example, treatment of gene lacking, treatment to stop the expression of the polypeptide by antisense DNA (RNA)). Genomic DNA may be isolated with the cDNA of the invention, as a probe. As the same manner, a human gene encoding which can be highly homologous to the cDNA of the invention, that is, which encodes a polypeptide highly homologous to the polypeptide of the invention and a gene of animals excluding mouse which can be highly homologous to the cDNA of the invention, also may be isolated.

[Application to Medicaments]

The polypeptide of the invention or the antibody specific for the polypeptide of the invention is administered systemically or topically and in general orally or parenterally for preventing or treating diseases related to incomplete growth or abnormal growth of hematopoietic system cells, acceleration or reduction of nerve system functions or acceleration or reduction of immune system functions, such as inflammatory diseases (e.g., rheumatoid, ulcerative colitis, etc.), cytopenia of hematopoietic stem cells after bone marrow transplantation, cytopenia of leukocytes, platelets, B cells or T cells after radiation treatment or after administration of a chemotherapeutic agent, anemia, infectious diseases, cancer, leukemia, AIDS, and various degenerative diseases (e.g., Alzheimer's disease, multiple sclerosis, etc.), or nerve damage, for preventing or treating metabolic disorder of bones (e.g., osteoporosis, or for repairing tissues. Oral administration, intravenous injection and intraventricular administration are preferred.

The doses to be administered depend upon age, body weight, symptom, desired therapeutic effect, route of administration, and duration of the treatment etc. In human adults, one dose per person is generally between 100 μg and 100 mg, by oral administration, up to several times per day, and between 10 μg and 100 mg, by parenteral administration up to several times per day.

As mentioned above, the doses to be used depend upon various conditions. Therefore, there are cases in which doses lower than or greater than the ranges specified above may be used.

The compounds of the invention, may be administered as solid compositions, liquid compositions or other compositions for oral administration, as injections, liniments or suppositories etc. for parenteral administration.

Solid compositions for oral administration include compressed tablets, pills, capsules, dispersible powders, granules. Capsules include soft or hard capsules.

In such compositions, one or more of the active compound(s) is or are admixed with at least one inert diluent (such as lactose, mannitol, glucose, hydroxypropyl cellulose, microcrystalline cellulose, starch, polyvinylpyrrolidone, magnesium metasilicate aluminate, etc.). The compositions may also comprise, as is normal practice, additional substances other than inert diluents: e.g. lubricating agents (such as magnesium stearate etc.), disintegrating agents (such as cellulose calcium glycolate, etc.), stabilizing agents (such as human serum albumin, lactose etc.), and assisting agents for dissolving (such as arginine, asparaginic acid etc.).

The tablets or pills may, if desired, be coated with a film of gastric or enteric materials (such as sugar, gelatin, hydroxypropyl cellulose or hydroxypropylmethyl cellulose phthalate, etc.), or be coated with more than two films. And then, coating may include containment within capsules of absorbable materials such as gelatin.

Liquid compositions for oral administration include pharmaceutically-acceptable emulsions, solutions, syrups and elixirs. In such compositions, one or more of the active compound(s) is or are contained in inert diluent(s) commonly used (purified water, ethanol etc.). Besides inert diluents, such compositions may also comprise adjuvants (such as wetting agents, suspending agents, etc.), sweetening agents, flavoring agents, perfuming agents, and preserving agents.

Other compositions for oral administration include spray compositions which may be prepared by known methods and which comprise one or more of the active compound(s). Spray compositions may comprise additional substances other than inert diluents: e.g. stabilizing agents (sodium sulfite etc.), isotonic buffer (sodium chloride, sodium citrate, citric acid, etc.). For preparation of such spray compositions, for example, the method described in the U.S. Pat. No. 2,868, 691 or 3,095,355 (herein incorporated in their entireties by reference) may be used.

Injections for parenteral administration include sterile aqueous or non-aqueous solutions, suspensions and emulsions. In such compositions, one or more active compound(s) is or are admixed with at least one inert aqueous diluent(s) (distilled water for injection, physiological salt solution, etc.) or inert non-aqueous diluents(s) (propylene glycol, polyethylene glycol, olive oil, ethanol, POLYSOLBATE 80™, etc.).

Injections may comprise additional compound other than inert diluents: e.g. preserving agents, wetting agents, emulsifying agents, dispersing agents, stabilizing agent (such as human serum albumin, lactose, etc.), and assisting agents such as assisting agents for dissolving (arginine, asparaginic acid, etc.).

BEST MODE CARRING OUT THE INVENTION

The invention are illustrated by the following examples, but not limit the invention.

Example

Total RNA was prepared from human bone marrow stromal cell line HAS303 (provided from Professor Keisuke Sotoyama, Dr. Makoto Aizawa, first medicine, Tokyo Medical College; See J. Cell. Physiol. 148: 245-251 (1991) and Experimental Hematol., 22: 482-487 (1994)) by TRIzol reagent (Trade Mark, GIBCOBRL). Poly(A) RNA was purified from the total RNA by mRNA purification kit (commercial name, Pharmacia).

Double strand cDNA was synthesized by SuperScript Plasmid System for cDNA Synthesis and Plasmid Cloning (brand name, GIBCOBRL) with above poly(A) RNA as template and random 9mer as primer which was containing XhoI site: SEQ ID NO. 9

5'-CGA TTG AAT TCT AGA CCT GCC TCG AGN NNN NNN NN-3' cDNA was ligated EcoRI adapter by DNA ligation kit ver. 2 (trade name, Takara Shuzo; this kit was used in all ligating steps hereafter) and digested by XhoI. cDNAs were separated by agarose-gel electrophoresis. 300-800 bp cDNAs were isolated and were ligated to EcoRI/NotI site of pSUC2 (see U.S. Pat. No. 5,536,637). *E. Coli* DH10B strain were transformed by pSUC2 with electropolation to obtain yeast SST cDNA library.

Plasmids of the cDNA library were prepared. Yeast YTK12 strain were transformed by the plasmids with lithium acetate method (Current Protocols In Molecular Biology 13.7.1). The transformed yeast were plated on triptphan-free medium (CMD-Try medium) for selection. The plate was incubated for 48 hour at 30° C. Replica of the colony which is obtained by Accutran Replica Plater (trade name, Schleicher & Schuell) were place YPR plate containing raffinose for carbon source, and the plate was incubated for 14 days at 30° C. After 3 days, each colony appeared was streaked on YPR plate again. The plates were incubated for 48 hours at 30° C. Single colony was inoculated to YPR medium and was incubated for 48 hours at 30° C. Then plasmids were prepared. Insert cDNA was amplified by PCR with two kind primers which exist end side of cloning site on pSUC2 (sense strand primers were biotinylated). Biotinylated single strand of cDNAs were purified with Dynabeads (trade name, DYNAL) and determined the nucleotide sequences. Sequencing was performed by Dye Terminator Cycle Sequencing Ready Reaction with DNA Sequencing kit (trade name, Applied Biosystems Inc.) and sequence was determined by DNA sequencer 373 (Applied Biosystems Inc.). All sequencing hereafter was carried with this method.

The clone named OAF065 is not registered on databases by homology search of nucleotide sequence and deduced amino acid sequence and so it is cleared that the sequence is novel one. We confirmed that OAF065 contains signal peptide in view of function and structure, by comparison with known peptide which has signal peptide and deduced amino acid sequence. Full length cDNA of OAF065 was isolated by 3'-RACE (Rapid Amplification of cDNA End). Marathon cDNA Amplification Kit (trade name, Clontech) was used in 3'-RACE. Adaptor-ligated double stranded cDNA was prepared from poly(A) RNA of HAS303 in line with the method of the kit. OAF065 specific primer F3 (28mer):

SEQ ID NO. 10
5'-AGA AAG ATG GCT TTA AAA GTG CTA CTA G-3' which included a deduced initiation ATG coden region based on the information of nucleotide sequence by SST was prepared. PCR was performed with the said primer and adapter primer attached in the kit. Two kinds of cDNAs (4.0 kb and 1.5 kb) were amplified and 4.0 kb-cDNA was named OAF065α and 1.5 kb-cDNA was named OAF0651β.

Two kinds cDNAs were separated with agarose-gel electrophoresis, and to pT7 Blue-2 T-Vector (trade name, Novagen), ligated in and transformed to *E. Coli* DH5α and then plasmid was prepared. Nucleotide sequences of 5'-end were determined, and the existence of nucleotide sequence OAF065 specific primer F3 were confirmed in both nucleotide sequences. 5'-End nucleotide sequence (ca 1.7 kb) of OAF065α and full length nucleotide sequence of OAF065β were determined and then obtained sequences shown in SEQ ID NOs 2 and 6. Open reading frame was searched and deduced amino acid sequences shown in SEQ ID NO. 4 and 8 were obtained.

Compared with the nucleotide sequences of OAF065α and OAF065β, nucleotide sequences from 1 to 1290 base were completely same, but sequences downstream from 1291 base had no homology each other. Compared with amino acid sequences of OAF065α and OAF065β, amino acids from 1 to 415 in N-termini were completely same, only two amino acids in C-termini of OAF065α were replaced to 8 amino acids (Val Arg Gln Arg Leu Gly Ser Leu) in the sequence of OAF065β. It was revealed that OAF065α and OAF065β were novel type-I membrane proteins by hydrophobicity analysis and that the extracellular region and the transmembrane region of both sequences were consistent.

The polypeptide OAF065α and OAF065β of the invention are not known one, when amino acid sequences of the polypeptide was compared by a computer to all known sequences in data base of Swiss Prot Release 33. Extracellular Cys rich region which commonly exists in the TNF receptor family was identified in the polypeptide of the invention.

That is, compared with amino acid sequences of the polypeptide of the invention (OAF065s) and other members of TNF receptor family i.e. human necrosis factor receptor 1 (hTNFR1), human necrosis factor receptor 2 (hTNFR2), human nerve growth factor receptor (hNGFR), and human Fas (hFas), it was revealed that the polypeptides (OAF065s) of the invention are type-I membrane protein and they have extracellular Cys rich region which commonly exists in the TNF (Tumor necrosis factor) receptor family in FIG. 1.

Therefore, it was confirmed that the polypeptides OAF065α and OAF065β of the invention are novel membrane proteins which belong to the TNF receptor family.

What is claimed is:

1. An isolated monoclonal or polyclonal antibody that specifically binds to a polypeptide selected from the group consisting of:

(a) a polypeptide comprising the amino acid sequence of SEQ ID NO:4;

(b) a polypeptide comprising the amino acid sequence of SEQ ID NO:8;

(c) a polypeptide comprising the amino acid sequence of residues 1 to 392 of SEQ ID NO:4;

(d) a polypeptide comprising the amino acid sequence of residues 1 to 398 of SEQ ID NO:8;

(e) a polypeptide comprising an amino acid sequence having at least 95% amino acid identity with the amino acid sequence of SEQ ID NO:4;
(f) a polypeptide comprising an amino acid sequence having at least 95% amino acid identity with the amino acid sequence of SEQ ID NO:8;
(g) a polypeptide comprising an amino acid sequence having at least 95% amino acid identity with the amino acid sequence of residues 1 to 392 of SEQ ID NO:4; and
(h) a polypeptide comprising an amino acid sequence having at least 95% amino acid identity with the amino acid sequence of residues 1 to 398 of SEQ ID NO:8;
wherein said polypeptides are TNF (tumor necrosis factor) receptor family members.

2. The isolated antibody according to claim 1, wherein said antibody specifically binds to a polypeptide comprising the amino acid sequence of SEQ ID NO:4.

3. The isolated antibody according to claim 1, wherein said antibody specifically binds to a polypeptide comprising the amino acid sequence of SEQ ID NO:8.

4. The isolated antibody according to claim 1, wherein said antibody specifically binds to a polypeptide comprising the amino acid sequence of residues 1 to 392 of SEQ ID NO:4.

5. The isolated antibody according to claim 1, wherein said antibody specifically binds to a polypeptide comprising the amino acid sequence of residues 1 to 398 of SEQ ID NO:8.

* * * * *

SEQUENCE LISTING

<160> NUMBER OF SEQ ID NOS: 15

<210> SEQ ID NO 1
<211> LENGTH: 1251
<212> TYPE: DNA
<213> ORGANISM: Homo Sapiens

<400> SEQUENCE: 1

```
atggctttaa aagtgctact agaacaagag aaaacgtttt tcactctttt agtattacta        60
ggctatttgt catgtaaagt gacttgtgaa acaggagact gtagacagca agaattcagg       120
gatcggtctg gaaactgtgt tccctgcaac cagtgtgggc caggcatgga gttgtctaag       180
gaatgtggct tcggctatgg ggaggatgca cagtgtgtga cgtgccggct gcacaggttc       240
```

```
aaggaggact gggcttcca gaaatgcaag ccctgtctgg actgcgcagt ggtgaaccgc    300
tttcagaagg caaattgttc agccaccagt gatgccatct gcggggactg cttgccagga    360
ttttatagga agacgaaact tgtcggcttt caagacatgg agtgtgtgcc ttgtggagac    420
cctcctcctc cttacgaacc gcactgtgcc agcaaggtca acctcgtgaa gatcgcgtcc    480
acggcctcca gcccacggga cacggcgctg gctgccgtta tctgcagcgc tctggccacc    540
gtcctgctgg ccctgctcat cctctgtgtc atctattgta agagacagtt tatggagaag    600
aaacccagct ggtctctgcg gtcacaggac attcagtaca cggctctga gctgtcgtgt    660 cttgacagac tcagctcca cgaatatgcc acagagcct gctgccagtg ccgccgtgac    720
tcagtgcaga cctgcgggcc ggtgcgcttg ctcccatcca tgtgctgtga ggaggcctgc    780
agccccaacc cggcgactct tggttgtggg gtgcattctg cagccagtct tcaggcaaga    840
aacgcaggcc cagccgggga gatggtgccg actttcttcg gatccctcac gcagtccatc    900
tgtggcgagt tttcagatgc ctggcctctg atgcagaatc ccatgggtgg tgacaacatc    960 tcttttgtg actcttatcc tgaactcact ggagaagaca ttcattctct caatccagaa   1020
cttgaaagct caacgtcttt ggattcaaat agcagtcaag atttggttgg tgggggctgtt   1080 ccagtccagt ctcattctga aaactttaca gcagctactg atttatctag atataacaac   1140
acactggtag aatcagcatc aactcaggat gcactaacta tgagaagcca gctagatcag   1200
gagagtggcg ctatcatcca cccagccact cagacgtccc tccaggaagc t            1251

<210> SEQ ID NO 2
<211> LENGTH: 1704
<212> TYPE: DNA
<213> ORGANISM: Homo sapiens

<400> SEQUENCE: 2
gggaacgtag aactctccaa caataaatac atttgataag aaagatggct ttaaaagtgc     60
tactagaaca agagaaaacg ttttcactc ttttagtatt actaggctat ttgtcatgta    120
aagtgacttg tgaaacagga gactgtagac agcaagaatt cagggatcgg tctggaaact    180
gtgttccctg caaccagtgt gggccaggca tggagttgtc taaggaatgt ggcttcggct    240
atggggagga tgcacagtgt gtgacgtgcc ggctgcacag gttcaaggag gactgggct    300 tccagaaatg caagccctgt ctggactgcg cagtggtgaa ccgctttcag aaggcaaatt    360
gttcagccac cagtgatgcc atctgcgggg actgcttgcc aggatttat aggaagacga    420 aacttgtcgg ctttcaagac atggagtgtg tgccttgtgg agaccctcct cctccttacg    480
aaccgcactg tgccagcaag gtcaacctcg tgaagatcgc gtccacggcc tccagcccac    540
gggacacggc gctggctgcc gttatctgca gcgctctggc caccgtcctg ctggccctgc    600
tcatcctctg tgtcatctat tgtaagagac agtttatgga agaaaccc agctggtctc    660 tgcggtcaca ggacattcag tacaacggct ctgagctgtc gtgtcttgac agacctcagc    720
tccacgaata tgcccacaga gcctgctgcc agtgccgccg tgactcagtg cagacctgcg    780
ggccggtgcg cttgctccca tccatgtgct gtgaggaggc ctgcagcccc aacccggcga    840
ctcttggttg tggggtgcat tctgcagcca gtcttcaggc aagaaacgca ggcccagccg    900
gggagatggt gccgactttc ttcggatccc tcacgcagtc catctgtggc gagttttcag    960
atgcctggcc tctgatgcag aatcccatgg gtggtgacaa catctctttt tgtgactctt   1020
atcctgaact cactggagaa gacattcatt ctctcaatcc agaacttgaa agctcaacgt   1080
ctttggattc aaatagcagt caagatttgg ttggtggggc tgttccagtc cagtctcatt   1140
```

-continued

```
ctgaaaactt tacagcagct actgatttat ctagatataa caacacactg gtagaatcag    1200
catcaactca ggatgcacta actatgagaa gccagctaga tcaggagagt ggcgctatca    1260
tccacccagc cactcagacg tccctccagg aagcttaaag aacctgcttc tttctgcagt    1320
agaagcgtgt gctggaaccc aaagagtact cctttgttag gcttatggac tgagcagtct    1380
ggaccttgca tggcttctgg ggcaaaaata atctgaacc aaactgacgg catttgaagc     1440
ctttcagcca gttgcttctg agccagacca gctgtaagct gaaacctcaa tgaataacaa    1500
gaaaagactc caggccgact catgatactc tgcatctttc ctacatgaga agcttctctg    1560
ccacaaaagt gacttcaaag acggatgggt tgagctggca gcctatgaga ttgtggacat    1620
ataacaagaa acagaaatgc cctcatgctt attttcatgg tgattgtggt tttacaagac    1680
tgaagaccca gagtatactt tttc                                            1704
```

<210> SEQ ID NO 3
<211> LENGTH: 1704
<212> TYPE: DNA
<213> ORGANISM: Homo sapiens
<220> FEATURE:
<221> NAME/KEY: misc_feature
<223> OTHER INFORMATION: Origin: human bone marrow stromal cell line HAS303
<220> FEATURE:
<221> NAME/KEY: CDS
<222> LOCATION: (45)..(1295)
<220> FEATURE:
<221> NAME/KEY: sig_peptide
<222> LOCATION: (45)..(119)
<220> FEATURE:
<221> NAME/KEY: mat_peptide
<222> LOCATION: (120)..(1295)

<400> SEQUENCE: 3

```
gggaacgtag aactctccaa caataaatac atttgataag aaag atg gct tta aaa       56
                                                 Met Ala Leu Lys
                                                    -25 gtg cta cta gaa caa gag aaa acg ttt ttc act ctt tta gta tta cta      104
Val Leu Leu Glu Gln Glu Lys Thr Phe Phe Thr Leu Leu Val Leu Leu
    -20                 -15                 -10 ggc tat ttg tca tgt aaa gtg act tgt gaa aca gga gac tgt aga cag      152
Gly Tyr Leu Ser Cys Lys Val Thr Cys Glu Thr Gly Asp Cys Arg Gln
 -5              -1   1               5                  10 caa gaa ttc agg gat cgg tct gga aac tgt gtt ccc tgc aac cag tgt      200
Gln Glu Phe Arg Asp Arg Ser Gly Asn Cys Val Pro Cys Asn Gln Cys
                15                  20                  25 ggg cca ggc atg gag ttg tct aag gaa tgt ggc ttc ggc tat ggg gag      248
Gly Pro Gly Met Glu Leu Ser Lys Glu Cys Gly Phe Gly Tyr Gly Glu
            30                  35                  40 gat gca cag tgt gtg acg tgc cgg ctg cac agg ttc aag gag gac tgg      296
Asp Ala Gln Cys Val Thr Cys Arg Leu His Arg Phe Lys Glu Asp Trp
        45                  50                  55 ggc ttc cag aaa tgc aag ccc tgt ctg gac tgc gca gtg gtg aac cgc      344
Gly Phe Gln Lys Cys Lys Pro Cys Leu Asp Cys Ala Val Val Asn Arg
    60                  65                  70                  75 ttt cag aag gca aat tgt tca gcc acc agt gat gcc atc tgc ggg gac      392
Phe Gln Lys Ala Asn Cys Ser Ala Thr Ser Asp Ala Ile Cys Gly Asp
                80                  85                  90 tgc ttg cca gga ttt tat agg aag acg aaa ctt gtc ggc ttt caa gac      440
Cys Leu Pro Gly Phe Tyr Arg Lys Thr Lys Leu Val Gly Phe Gln Asp
            95                  100                 105 atg gag tgt gtg cct tgt gga gac cct cct cct cct tac gaa ccg cac      488
Met Glu Cys Val Pro Cys Gly Asp Pro Pro Pro Pro Tyr Glu Pro His
        110                 115                 120
```

```
                                                             -continued tgt gcc agc aag gtc aac ctc gtg aag atc gcg tcc acg gcc tcc agc        536
Cys Ala Ser Lys Val Asn Leu Val Lys Ile Ala Ser Thr Ala Ser Ser
125                 130                 135 cca cgg gac acg gcg ctg gct gcc gtt atc tgc agc gct ctg gcc acc        584
Pro Arg Asp Thr Ala Leu Ala Ala Val Ile Cys Ser Ala Leu Ala Thr
140                 145                 150                 155 gtc ctg ctg gcc ctg ctc atc ctc tgt gtc atc tat tgt aag aga cag        632
Val Leu Leu Ala Leu Leu Ile Leu Cys Val Ile Tyr Cys Lys Arg Gln
                160                 165                 170 ttt atg gag aag aaa ccc agc tgg tct ctg cgg tca cag gac att cag        680
Phe Met Glu Lys Lys Pro Ser Trp Ser Leu Arg Ser Gln Asp Ile Gln
            175                 180                 185 tac aac ggc tct gag ctg tcg tgt ctt gac aga cct cag ctc cac gaa        728
Tyr Asn Gly Ser Glu Leu Ser Cys Leu Asp Arg Pro Gln Leu His Glu
        190                 195                 200 tat gcc cac aga gcc tgc tgc cag tgc cgc cgt gac tca gtg cag acc        776
Tyr Ala His Arg Ala Cys Cys Gln Cys Arg Arg Asp Ser Val Gln Thr
    205                 210                 215 tgc ggg ccg gtg cgc ttg ctc cca tcc atg tgc tgt gag gag gcc tgc        824
Cys Gly Pro Val Arg Leu Leu Pro Ser Met Cys Cys Glu Glu Ala Cys
220                 225                 230                 235 agc ccc aac ccg gcg act ctt ggt tgt ggg gtg cat tct gca gcc agt        872
Ser Pro Asn Pro Ala Thr Leu Gly Cys Gly Val His Ser Ala Ala Ser
                240                 245                 250 ctt cag gca aga aac gca ggc cca gcc ggg gag atg gtg ccg act ttc        920
Leu Gln Ala Arg Asn Ala Gly Pro Ala Gly Glu Met Val Pro Thr Phe
            255                 260                 265 ttc gga tcc ctc acg cag tcc atc tgt ggc gag ttt tca gat gcc tgg        968
Phe Gly Ser Leu Thr Gln Ser Ile Cys Gly Glu Phe Ser Asp Ala Trp
        270                 275                 280 cct ctg atg cag aat ccc atg ggt ggt gac aac atc tct ttt tgt gac       1016
Pro Leu Met Gln Asn Pro Met Gly Gly Asp Asn Ile Ser Phe Cys Asp
    285                 290                 295 tct tat cct gaa ctc act gga gaa gac att cat tct ctc aat cca gaa       1064
Ser Tyr Pro Glu Leu Thr Gly Glu Asp Ile His Ser Leu Asn Pro Glu
300                 305                 310                 315 ctt gaa agc tca acg tct ttg gat tca aat agc agt caa gat ttg gtt       1112
Leu Glu Ser Ser Thr Ser Leu Asp Ser Asn Ser Ser Gln Asp Leu Val
                320                 325                 330 ggt ggg gct gtt cca gtc cag tct cat tct gaa aac ttt aca gca gct       1160
Gly Gly Ala Val Pro Val Gln Ser His Ser Glu Asn Phe Thr Ala Ala
            335                 340                 345 act gat tta tct aga tat aac aac aca ctg gta gaa tca gca tca act       1208
Thr Asp Leu Ser Arg Tyr Asn Asn Thr Leu Val Glu Ser Ala Ser Thr
        350                 355                 360 cag gat gca cta act atg aga agc cag cta gat cag gag agt ggc gct       1256
Gln Asp Ala Leu Thr Met Arg Ser Gln Leu Asp Gln Glu Ser Gly Ala
    365                 370                 375 atc atc cac cca gcc act cag acg tcc ctc cag gaa gct taaagaacct        1305
Ile Ile His Pro Ala Thr Gln Thr Ser Leu Gln Glu Ala
380                 385                 390 gcttctttct gcagtagaag cgtgtgctgg aacccaaaga gtactccttt gttaggctta     1365
tggactgagc agtctggacc ttgcatggct tctggggcaa aaataaatct gaaccaaact     1425
gacggcattt gaagcctttc agccagttgc ttctgagcca accagctgt aagctgaaac      1485 ctcaatgaat aacaagaaaa gactccaggc cgactcatga tactctgcat ctttcctaca     1545
tgagaagctt ctctgccaca aaagtgactt caaagacgga tgggttgagc tggcagccta     1605
tgagattgtg gacatataac aagaaacaga aatgccctca tgcttatttt catggtgatt    1665
```

-continued

```
gtggttttac aagactgaag acccagagta tactttttc                    1704
```

<210> SEQ ID NO 4
<211> LENGTH: 417
<212> TYPE: PRT
<213> ORGANISM: Homo sapiens
<220> FEATURE:
<221> NAME/KEY: misc_feature
<223> OTHER INFORMATION: Origin: human bone marrow stromal cell line
      HAS303

<400> SEQUENCE: 4

| Met | Ala | Leu | Lys | Val | Leu | Leu | Glu | Gln | Glu | Lys | Thr | Phe | Phe | Thr | Leu |
| -25 | | | | -20 | | | | -15 | | | | | | | -10 |

| Leu | Val | Leu | Leu | Gly | Tyr | Leu | Ser | Cys | Lys | Val | Thr | Cys | Glu | Thr | Gly |
| | | | -5 | | | | | -1 | 1 | | | | 5 | | |

| Asp | Cys | Arg | Gln | Gln | Glu | Phe | Arg | Asp | Arg | Ser | Gly | Asn | Cys | Val | Pro |
| | | 10 | | | | | 15 | | | | | 20 | | | |

| Cys | Asn | Gln | Cys | Gly | Pro | Gly | Met | Glu | Leu | Ser | Lys | Glu | Cys | Gly | Phe |
| | 25 | | | | | 30 | | | | | 35 | | | | |

| Gly | Tyr | Gly | Glu | Asp | Ala | Gln | Cys | Val | Thr | Cys | Arg | Leu | His | Arg | Phe |
| 40 | | | | | 45 | | | | | 50 | | | | | 55 |

| Lys | Glu | Asp | Trp | Gly | Phe | Gln | Lys | Cys | Lys | Pro | Cys | Leu | Asp | Cys | Ala |
| | | | | 60 | | | | | 65 | | | | | 70 | |

| Val | Val | Asn | Arg | Phe | Gln | Lys | Ala | Asn | Cys | Ser | Ala | Thr | Ser | Asp | Ala |
| | | | 75 | | | | | 80 | | | | | 85 | | |

| Ile | Cys | Gly | Asp | Cys | Leu | Pro | Gly | Phe | Tyr | Arg | Lys | Thr | Lys | Leu | Val |
| | | 90 | | | | | 95 | | | | | 100 | | | |

| Gly | Phe | Gln | Asp | Met | Glu | Cys | Val | Pro | Cys | Gly | Asp | Pro | Pro | Pro | Pro |
| | 105 | | | | | 110 | | | | | 115 | | | | |

| Tyr | Glu | Pro | His | Cys | Ala | Ser | Lys | Val | Asn | Leu | Val | Lys | Ile | Ala | Ser |
| 120 | | | | | 125 | | | | | 130 | | | | | 135 |

| Thr | Ala | Ser | Ser | Pro | Arg | Asp | Thr | Ala | Leu | Ala | Ala | Val | Ile | Cys | Ser |
| | | | | 140 | | | | | 145 | | | | | 150 | |

| Ala | Leu | Ala | Thr | Val | Leu | Leu | Ala | Leu | Leu | Ile | Leu | Cys | Val | Ile | Tyr |
| | | | 155 | | | | | 160 | | | | | 165 | | |

| Cys | Lys | Arg | Gln | Phe | Met | Glu | Lys | Lys | Pro | Ser | Trp | Ser | Leu | Arg | Ser |
| | | 170 | | | | | 175 | | | | | 180 | | | |

| Gln | Asp | Ile | Gln | Tyr | Asn | Gly | Ser | Glu | Leu | Ser | Cys | Leu | Asp | Arg | Pro |
| | 185 | | | | | 190 | | | | | 195 | | | | |

| Gln | Leu | His | Glu | Tyr | Ala | His | Arg | Ala | Cys | Cys | Gln | Cys | Arg | Arg | Asp |
| 200 | | | | | 205 | | | | | 210 | | | | | 215 |

| Ser | Val | Gln | Thr | Cys | Gly | Pro | Val | Arg | Leu | Leu | Pro | Ser | Met | Cys | Cys |
| | | | | 220 | | | | | 225 | | | | | 230 | |

| Glu | Glu | Ala | Cys | Ser | Pro | Asn | Pro | Ala | Thr | Leu | Gly | Cys | Gly | Val | His |
| | | | 235 | | | | | 240 | | | | | 245 | | |

| Ser | Ala | Ala | Ser | Leu | Gln | Ala | Arg | Asn | Ala | Gly | Pro | Ala | Gly | Glu | Met |
| | | 250 | | | | | 255 | | | | | 260 | | | |

| Val | Pro | Thr | Phe | Phe | Gly | Ser | Leu | Thr | Gln | Ser | Ile | Cys | Gly | Glu | Phe |
| | 265 | | | | | 270 | | | | | 275 | | | | |

| Ser | Asp | Ala | Trp | Pro | Leu | Met | Gln | Asn | Pro | Met | Gly | Gly | Asp | Asn | Ile |
| 280 | | | | | 285 | | | | | 290 | | | | | 295 |

| Ser | Phe | Cys | Asp | Ser | Tyr | Pro | Glu | Leu | Thr | Gly | Glu | Asp | Ile | His | Ser |
| | | | 300 | | | | | 305 | | | | | 310 | | |

| Leu | Asn | Pro | Glu | Leu | Glu | Ser | Ser | Thr | Ser | Leu | Asp | Ser | Asn | Ser | Ser |
| | | | 315 | | | | | 320 | | | | | 325 | | |

Gln Asp Leu Val Gly Gly Ala Val Pro Val Gln Ser His Ser Glu Asn
            330                 335                 340

Phe Thr Ala Ala Thr Asp Leu Ser Arg Tyr Asn Asn Thr Leu Val Glu
        345                 350                 355

Ser Ala Ser Thr Gln Asp Ala Leu Thr Met Arg Ser Gln Leu Asp Gln
360                 365                 370                 375

Glu Ser Gly Ala Ile Ile His Pro Ala Thr Gln Thr Ser Leu Gln Glu
            380                 385                 390

Ala

<210> SEQ ID NO 5
<211> LENGTH: 1269
<212> TYPE: DNA
<213> ORGANISM: Homo sapiens

<400> SEQUENCE: 5

| | |
|---|---|
| atggctttaa aagtgctact agaacaagag aaaacgtttt tcactctttt agtattacta | 60 |
| ggctatttgt catgtaaagt gacttgtgaa acaggagact gtagacagca agaattcagg | 120 |
| gatcggtctg gaaactgtgt tccctgcaac cagtgtgggc caggcatgga gttgtctaag | 180 |
| gaatgtggct tcggctatgg ggaggatgca cagtgtgtga cgtgccggct gcacaggttc | 240 |
| aaggaggact ggggcttcca gaaatgcaag ccctgtctgg actgcgcagt ggtgaaccgc | 300 |
| tttcagaagg caaattgttc agccaccagt gatgccatct gcggggactg cttgccagga | 360 |
| ttttatagga gacgaaaact tgtcggcttt caagacatgg agtgtgtgcc ttgtggagac | 420 |
| cctcctcctc cttacgaacc gcactgtgcc agcaaggtca acctcgtgaa gatcgcgtcc | 480 |
| acggcctcca gcccacggga cacggcgctg gctgccgtta tctgcagcgc tctggccacc | 540 |
| gtcctgctgg ccctgctcat cctctgtgtc atctattgta agagacagtt tatggagaag | 600 |
| aaacccagct ggtctctgcg gtcacaggac attcagtaca acggctctga gctgtcgtgt | 660 |
| cttgacagac ctcagctcca cgaatatgcc cacagagcct gctgccagtg ccgccgtgac | 720 |
| tcagtgcaga cctgcgggcc ggtgcgcttg ctcccatcca tgtgctgtga ggaggcctgc | 780 |
| agccccaacc cggcgactct tggttgtggg gtgcattctg cagccagtct tcaggcaaga | 840 |
| aacgcaggcc cagccgggga gatggtgccg actttcttcg gatccctcac gcagtccatc | 900 |
| tgtggcgagt tttcagatgc ctggcctctg atgcagaatc ccatgggtgg tgacaacatc | 960 |
| tcttttgtg actcttatcc tgaactcact ggagaagaca ttcattctct caatccagaa | 1020 |
| cttgaaagct caacgtcttt ggattcaaat agcagtcaag atttggttgg tgggctgtt | 1080 |
| ccagtccagt ctcattctga aactttaca gcagctactg attatctag atataacaac | 1140 |
| acactggtag aatcagcatc aactcaggat gcactaacta tgagaagcca gctagatcag | 1200 |
| gagagtggcg ctatcatcca cccagccact cagacgtccc tccaggtaag gcagcgactg | 1260 |
| ggttccctg | 1269 |

<210> SEQ ID NO 6
<211> LENGTH: 1496
<212> TYPE: DNA
<213> ORGANISM: Homo sapiens

<400> SEQUENCE: 6

| | |
|---|---|
| gggaacgtag aactctccaa caataaatac atttgataag aaagatggct ttaaaagtgc | 60 |
| tactagaaca agagaaaacg ttttccactc ttttagtatt actaggctat tgtcatgta | 120 |
| aagtgacttg tgaaacagga gactgtagac agcaagaatt cagggatcgg tctggaaact | 180 |

-continued

```
gtgttccctg caaccagtgt gggccaggca tggagttgtc taaggaatgt ggcttcggct    240
atggggagga tgcacagtgt gtgacgtgcc ggctgcacag gttcaaggag gactgggct    300 tccagaaatg caagccctgt ctggactgcg cagtggtgaa ccgctttcag aaggcaaatt    360
gttcagccac cagtgatgcc atctgcgggg actgcttgcc aggatttat aggaagacga    420 aacttgtcgg ctttcaagac atggagtgtg tgccttgtgg agaccctcct cctccttacg    480
aaccgcactg tgccagcaag gtcaacctcg tgaagatcgc gtccacggcc tccagcccac    540
gggacacggc gctggctgcc gttatctgca gcgctctggc caccgtcctg ctggccctgc    600
tcatcctctg tgtcatctat tgtaagagac agtttatgga aagaaaccc agctggtctc    660 tgcggtcaca ggacattcag tacaacggct ctgagctgtc gtgtcttgac agacctcagc    720
tccacgaata tgcccacaga gcctgctgcc agtgccgccg tgactcagtg cagacctgcg    780
ggccggtgcg cttgctccca tccatgtgct gtgaggaggc ctgcagcccc aacccggcga    840
ctcttggttg tggggtgcat tctgcagcca gtcttcaggc aagaaacgca ggcccagccg    900
gggagatggt gccgactttc ttcggatccc tcacgcagtc catctgtggc gagttttcag    960
atgcctggcc tctgatgcag aatcccatgg gtggtgacaa catctctttt tgtgactctt   1020
atcctgaact cactggagaa gacattcatt ctctcaatcc agaacttgaa agctcaacgt   1080
ctttggattc aaatagcagt caagatttgg ttggtgggc tgttccagtc cagtctcatt   1140
ctgaaaactt tacagcagct actgatttat ctagatataa caacacactg gtagaatcag   1200
catcaactca ggatgcacta actatgagaa gccagctaga tcaggagagt ggcgctatca   1260
tccacccagc cactcagacg tccctccagg taaggcagcg actgggttcc ctgtgaacac   1320
agcactgact tacagtagat cagaactctg ttcccagcat aagatttggg ggaacctgat   1380 gagtttttt tttgcatctt taataatttc ttgtatgttg tagagtatgt tttaaaataa   1440
atttcaagta ttttttttaa aaactaaaaa aaaaaaaaaa aaaaaaaaaa aaaaaa      1496
```

<210> SEQ ID NO 7
<211> LENGTH: 1496
<212> TYPE: DNA
<213> ORGANISM: Homo sapiens
<220> FEATURE:
<221> NAME/KEY: misc_feature
<223> OTHER INFORMATION: Origin: human bone marrow stromal cell line HAS303
<220> FEATURE:
<221> NAME/KEY: CDS
<222> LOCATION: (45)..(1313)
<220> FEATURE:
<221> NAME/KEY: sig_peptide
<222> LOCATION: (45)..(119)
<220> FEATURE:
<221> NAME/KEY: mat_peptide
<222> LOCATION: (120)..()

<400> SEQUENCE: 7

```
gggaacgtag aactctccaa caataaatac atttgataag aaag atg gct tta aaa         56
                                                Met Ala Leu Lys
                                                    -25 gtg cta cta gaa caa gag aaa acg ttt ttc act ctt tta gta tta cta       104
Val Leu Leu Glu Gln Glu Lys Thr Phe Phe Thr Leu Leu Val Leu Leu
    -20                 -15                 -10 ggc tat ttg tca tgt aaa gtg act tgt gaa aca gga gac tgt aga cag       152
Gly Tyr Leu Ser Cys Lys Val Thr Cys Glu Thr Gly Asp Cys Arg Gln
 -5              -1  1               5                  10 caa gaa ttc agg gat cgg tct gga aac tgt gtt ccc tgc aac cag tgt       200
Gln Glu Phe Arg Asp Arg Ser Gly Asn Cys Val Pro Cys Asn Gln Cys
```

```
            15                  20                  25
ggg cca ggc atg gag ttg tct aag gaa tgt ggc ttc ggc tat ggg gag   248
Gly Pro Gly Met Glu Leu Ser Lys Glu Cys Gly Phe Gly Tyr Gly Glu
         30                  35                  40 gat gca cag tgt gtg acg tgc cgg ctg cac agg ttc aag gag gac tgg   296
Asp Ala Gln Cys Val Thr Cys Arg Leu His Arg Phe Lys Glu Asp Trp
 45                  50                  55 ggc ttc cag aaa tgc aag ccc tgt ctg gac tgc gca gtg gtg aac cgc   344
Gly Phe Gln Lys Cys Lys Pro Cys Leu Asp Cys Ala Val Val Asn Arg
 60                  65                  70                  75 ttt cag aag gca aat tgt tca gcc acc agt gat gcc atc tgc ggg gac   392
Phe Gln Lys Ala Asn Cys Ser Ala Thr Ser Asp Ala Ile Cys Gly Asp
                 80                  85                  90 tgc ttg cca gga ttt tat agg aag acg aaa ctt gtc ggc ttt caa gac   440
Cys Leu Pro Gly Phe Tyr Arg Lys Thr Lys Leu Val Gly Phe Gln Asp
             95                 100                 105 atg gag tgt gtg cct tgt gga gac cct cct cct cct tac gaa ccg cac   488
Met Glu Cys Val Pro Cys Gly Asp Pro Pro Pro Pro Tyr Glu Pro His
         110                 115                 120 tgt gcc agc aag gtc aac ctc gtg aag atc gcg tcc acg gcc tcc agc   536
Cys Ala Ser Lys Val Asn Leu Val Lys Ile Ala Ser Thr Ala Ser Ser
     125                 130                 135 cca cgg gac acg gcg ctg gct gcc gtt atc tgc agc gct ctg gcc acc   584
Pro Arg Asp Thr Ala Leu Ala Ala Val Ile Cys Ser Ala Leu Ala Thr
140                 145                 150                 155 gtc ctg ctg gcc ctg ctc atc ctc tgt gtc atc tat tgt aag aga cag   632
Val Leu Leu Ala Leu Leu Ile Leu Cys Val Ile Tyr Cys Lys Arg Gln
                 160                 165                 170 ttt atg gag aag aaa ccc agc tgg tct ctg cgg tca cag gac att cag   680
Phe Met Glu Lys Lys Pro Ser Trp Ser Leu Arg Ser Gln Asp Ile Gln
             175                 180                 185 tac aac ggc tct gag ctg tcg tgt ctt gac aga cct cag ctc cac gaa   728
Tyr Asn Gly Ser Glu Leu Ser Cys Leu Asp Arg Pro Gln Leu His Glu
         190                 195                 200 tat gcc cac aga gcc tgc tgc cag tgc cgc cgt gac tca gtg cag acc   776
Tyr Ala His Arg Ala Cys Cys Gln Cys Arg Arg Asp Ser Val Gln Thr
     205                 210                 215 tgc ggg ccg gtg cgc ttg ctc cca tcc atg tgc tgt gag gag gcc tgc   824
Cys Gly Pro Val Arg Leu Leu Pro Ser Met Cys Cys Glu Glu Ala Cys
220                 225                 230                 235 agc ccc aac ccg gcg act ctt ggt tgt ggg gtg cat tct gca gcc agt   872
Ser Pro Asn Pro Ala Thr Leu Gly Cys Gly Val His Ser Ala Ala Ser
                 240                 245                 250 ctt cag gca aga aac gca ggc cca gcc ggg gag atg gtg ccg act ttc   920
Leu Gln Ala Arg Asn Ala Gly Pro Ala Gly Glu Met Val Pro Thr Phe
             255                 260                 265 ttc gga tcc ctc acg cag tcc atc tgt ggc gag ttt tca gat gcc tgg   968
Phe Gly Ser Leu Thr Gln Ser Ile Cys Gly Glu Phe Ser Asp Ala Trp
         270                 275                 280 cct ctg atg cag aat ccc atg ggt ggt gac aac atc tct ttt tgt gac  1016
Pro Leu Met Gln Asn Pro Met Gly Gly Asp Asn Ile Ser Phe Cys Asp
     285                 290                 295 tct tat cct gaa ctc act gga gaa gac att cat tct ctc aat cca gaa  1064
Ser Tyr Pro Glu Leu Thr Gly Glu Asp Ile His Ser Leu Asn Pro Glu
300                 305                 310                 315 ctt gaa agc tca acg tct ttg gat tca aat agc agt caa gat ttg gtt  1112
Leu Glu Ser Ser Thr Ser Leu Asp Ser Asn Ser Ser Gln Asp Leu Val
                 320                 325                 330 ggt ggg gct gtt cca gtc cag tct cat tct gaa aac ttt aca gca gct  1160
Gly Gly Ala Val Pro Val Gln Ser His Ser Glu Asn Phe Thr Ala Ala
```

```
                 335                 340                 345
act gat tta tct aga tat aac aac aca ctg gta gaa tca gca tca act   1208
Thr Asp Leu Ser Arg Tyr Asn Asn Thr Leu Val Glu Ser Ala Ser Thr
        350                 355                 360 cag gat gca cta act atg aga agc cag cta gat cag gag agt ggc gct   1256
Gln Asp Ala Leu Thr Met Arg Ser Gln Leu Asp Gln Glu Ser Gly Ala
365                 370                 375 atc atc cac cca gcc act cag acg tcc ctc cag gta agg cag cga ctg   1304
Ile Ile His Pro Ala Thr Gln Thr Ser Leu Gln Val Arg Gln Arg Leu
380                 385                 390                 395 ggt tcc ctg tgaacacagc actgacttac agtagatcag aactctgttc           1353
Gly Ser Leu ccagcataag atttgggga acctgatgag ttttttttt gcatctttaa taatttcttg   1413
tatgttgtag agtatgtttt aaaataaatt tcaagtattt ttttaaaaa ctaaaaaaaa  1473 aaaaaaaaaa aaaaaaaaa aaa                                          1496

<210> SEQ ID NO 8
<211> LENGTH: 423
<212> TYPE: PRT
<213> ORGANISM: Homo sapiens
<220> FEATURE:
<221> NAME/KEY: misc_feature
<223> OTHER INFORMATION: Origin: human bone marrow stromal cell line
      HAS303

<400> SEQUENCE: 8

Met Ala Leu Lys Val Leu Leu Glu Gln Glu Lys Thr Phe Phe Thr Leu
-25                 -20                 -15                 -10

Leu Val Leu Leu Gly Tyr Leu Ser Cys Lys Val Thr Cys Glu Thr Gly
            -5                  -1  1                   5

Asp Cys Arg Gln Gln Glu Phe Arg Asp Arg Ser Gly Asn Cys Val Pro
                10                  15                  20

Cys Asn Gln Cys Gly Pro Gly Met Glu Leu Ser Lys Glu Cys Gly Phe
        25                  30                  35

Gly Tyr Gly Glu Asp Ala Gln Cys Val Thr Cys Arg Leu His Arg Phe
40                  45                  50                  55

Lys Glu Asp Trp Gly Phe Gln Lys Cys Lys Pro Cys Leu Asp Cys Ala
                60                  65                  70

Val Val Asn Arg Phe Gln Lys Ala Asn Cys Ser Ala Thr Ser Asp Ala
        75                  80                  85

Ile Cys Gly Asp Cys Leu Pro Gly Phe Tyr Arg Lys Thr Lys Leu Val
        90                  95                  100

Gly Phe Gln Asp Met Glu Cys Val Pro Cys Gly Asp Pro Pro Pro Pro
    105                 110                 115

Tyr Glu Pro His Cys Ala Ser Lys Val Asn Leu Val Lys Ile Ala Ser
120                 125                 130                 135

Thr Ala Ser Ser Pro Arg Asp Thr Ala Leu Ala Ala Val Ile Cys Ser
                140                 145                 150

Ala Leu Ala Thr Val Leu Leu Ala Leu Leu Ile Leu Cys Val Ile Tyr
        155                 160                 165

Cys Lys Arg Gln Phe Met Glu Lys Lys Pro Ser Trp Ser Leu Arg Ser
        170                 175                 180

Gln Asp Ile Gln Tyr Asn Gly Ser Glu Leu Ser Cys Leu Asp Arg Pro
    185                 190                 195

Gln Leu His Glu Tyr Ala His Arg Ala Cys Cys Gln Cys Arg Arg Asp
200                 205                 210                 215
```

```
Ser Val Gln Thr Cys Gly Pro Val Arg Leu Leu Pro Ser Met Cys Cys
            220                 225                 230
Glu Glu Ala Cys Ser Pro Asn Pro Ala Thr Leu Gly Cys Gly Val His
            235                 240                 245
Ser Ala Ser Leu Gln Ala Arg Asn Ala Gly Pro Ala Gly Glu Met
            250                 255                 260
Val Pro Thr Phe Phe Gly Ser Leu Thr Gln Ser Ile Cys Gly Glu Phe
265                 270                 275
Ser Asp Ala Trp Pro Leu Met Gln Asn Pro Met Gly Gly Asp Asn Ile
280                 285                 290                 295
Ser Phe Cys Asp Ser Tyr Pro Glu Leu Thr Gly Glu Asp Ile His Ser
                300                 305                 310
Leu Asn Pro Glu Leu Glu Ser Ser Thr Ser Leu Asp Ser Asn Ser Ser
            315                 320                 325
Gln Asp Leu Val Gly Gly Ala Val Pro Val Gln Ser His Ser Glu Asn
            330                 335                 340
Phe Thr Ala Ala Thr Asp Leu Ser Arg Tyr Asn Asn Thr Leu Val Glu
            345                 350                 355
Ser Ala Ser Thr Gln Asp Ala Leu Thr Met Arg Ser Gln Leu Asp Gln
360                 365                 370                 375
Glu Ser Gly Ala Ile Ile His Pro Ala Thr Gln Thr Ser Leu Gln Val
                380                 385                 390
Arg Gln Arg Leu Gly Ser Leu
            395

<210> SEQ ID NO 9
<211> LENGTH: 35
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 27..35
<223> OTHER INFORMATION: n can be any nucleotide

<400> SEQUENCE: 9
cgattgaatt ctagacctgc ctcgagnnnn nnnnn                              35

<210> SEQ ID NO 10
<211> LENGTH: 28
<212> TYPE: DNA
<213> ORGANISM: Artificial Sequence
<220> FEATURE:
<223> OTHER INFORMATION: Primer 0AF065

<400> SEQUENCE: 10
agaaagatgg ctttaaaagt gctactag                                     28

<210> SEQ ID NO 11
<211> LENGTH: 122
<212> TYPE: PRT
<213> ORGANISM: Artificial Sequence
<220> FEATURE:
<223> OTHER INFORMATION: Amino acid sequence of 0AF065s

<400> SEQUENCE: 11

Met Ala Leu Lys Val Leu Leu Glu Gln Glu Lys Thr Phe Phe Thr Leu
1               5                   10                  15
Leu Val Leu Gly Tyr Leu Ser Cys Lys Val Thr Cys Glu Thr Gly
            20                  25                  30
```

```
Asp Cys Arg Gln Gln Glu Phe Arg Asp Arg Ser Gly Asn Cys Val Pro
            35                  40                  45

Cys Asn Gln Cys Gly Pro Gly Met Glu Leu Ser Lys Glu Cys Gly Phe
    50                  55                  60

Gly Tyr Gly Glu Asp Ala Gln Cys Val Thr Cys Arg Leu His Arg Phe
65                  70                  75                  80

Lys Glu Asp Trp Gly Phe Gln Lys Cys Lys Pro Cys Leu Asp Cys Ala
                85                  90                  95

Val Val Asn Arg Phe Gln Lys Ala Asn Cys Ser Ala Thr Ser Asp Ala
                100                 105                 110

Ile Cys Gly Asp Cys Leu Pro Gly Phe Tyr
            115                 120

<210> SEQ ID NO 12
<211> LENGTH: 132
<212> TYPE: PRT
<213> ORGANISM: Homo sapiens

<400> SEQUENCE: 12

Met Gly Leu Ser Thr Val Pro Asp Leu Leu Pro Leu Val Leu Leu
1               5                   10                  15

Glu Leu Leu Val Gly Ile Tyr Pro Ser Gly Val Ile Gly Leu Val Pro
                20                  25                  30

His Leu Gly Asp Arg Glu Lys Arg Asp Ser Val Cys Pro Gln Gly Lys
                35                  40                  45

Tyr Ile His Pro Gln Asn Asn Ser Ile Cys Cys Thr Lys Cys His Lys
            50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
                100                 105                 110

Glu Ile Ser Ser Cys Thr Val Asp Arg Asp Thr Val Cys Gly Cys Arg
                115                 120                 125

Lys Asn Gln Tyr
        130

<210> SEQ ID NO 13
<211> LENGTH: 125
<212> TYPE: PRT
<213> ORGANISM: Homo sapiens

<400> SEQUENCE: 13

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
                20                  25                  30

Ala Pro Glu Pro Gly Ser Thr Cys Arg Leu Arg Glu Tyr Tyr Asp Gln
            35                  40                  45

Thr Ala Gln Met Cys Cys Ser Lys Cys Ser Pro Gly Gln His Ala Lys
        50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
```

```
                   100                  105                 110
Glu Gln Asn Arg Ile Cys Thr Cys Arg Pro Gly Trp Tyr
        115                 120                 125

<210> SEQ ID NO 14
<211> LENGTH: 114
<212> TYPE: PRT
<213> ORGANISM: Homo sapiens

<400> SEQUENCE: 14

Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
            20                  25                  30

Pro Thr Gly Leu Tyr Thr His Ser Gly Glu Cys Cys Lys Ala Cys Asn
        35                  40                  45

Leu Gly Glu Gly Val Ala Gln Pro Cys Gly Ala Asn Gln Thr Val Cys
    50                  55                  60

Glu Pro Cys Leu Asp Ser Val Thr Phe Ser Asp Val Val Ser Ala Thr
65                  70                  75                  80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
            100                 105                 110

Tyr Tyr

<210> SEQ ID NO 15
<211> LENGTH: 134
<212> TYPE: PRT
<213> ORGANISM: Homo sapiens

<400> SEQUENCE: 15

Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe
    130
```